United States Patent
Kawamura

(10) Patent No.: US 8,740,858 B2
(45) Date of Patent: Jun. 3, 2014

(54) SYRINGE KIT FOR MIXING TWO MEDICINAL FLUIDS

(71) Applicant: Daikyo Seiko, Ltd., Tokyo (JP)

(72) Inventor: Hideaki Kawamura, Tokyo (JP)

(73) Assignee: Daikyo Seiko, Ltd., Tokyo (JP)

( * ) Notice: Subject to any disclaimer, the term of this patent is extended or adjusted under 35 U.S.C. 154(b) by 0 days.

(21) Appl. No.: 13/709,893

(22) Filed: Dec. 10, 2012

(65) Prior Publication Data
US 2013/0165853 A1 Jun. 27, 2013

(30) Foreign Application Priority Data
Dec. 26, 2011 (JP) ................................. 2011-283255

(51) Int. Cl.
*A61M 5/31* (2006.01)
(52) U.S. Cl.
USPC .......................................................... 604/243
(58) Field of Classification Search
USPC .......................................... 604/82, 243, 534
See application file for complete search history.

(56) References Cited

U.S. PATENT DOCUMENTS

| | | | |
|---|---|---|---|
| 5,851,201 A | | 12/1998 | Ritger et al. |
| 2001/0016703 A1 | | 8/2001 | Wironen et al. |
| 2001/0037091 A1 | * | 11/2001 | Wironen et al. ............. 604/236 |
| 2005/0119609 A1 | * | 6/2005 | McLean .......................... 604/82 |
| 2009/0177186 A1 | * | 7/2009 | Delano ......................... 604/534 |
| 2010/0280462 A1 | * | 11/2010 | Kommireddy et al. ....... 604/243 |

FOREIGN PATENT DOCUMENTS

| | | | | |
|---|---|---|---|---|
| EP | 1 080 742 A1 | | 3/2001 | |
| EP | 1080742 A1 | * | 3/2001 | ............ A61M 5/142 |
| JP | 2003-518411 A | | 6/2003 | |

OTHER PUBLICATIONS

European Patent Office, "European Search Report for EP 12 197 225.1", Apr. 2013.

* cited by examiner

*Primary Examiner* — Nicholas Lucchesi
*Assistant Examiner* — Diva K Chander
(74) *Attorney, Agent, or Firm* — Manabu Kanesaka

(57) ABSTRACT

A syringe kit for mixing two medicinal fluids includes first and second barrels containing medicinal fluids therein. The first barrel includes a connecting tube portion at a tip portion having a male screw on an outer periphery, and a non-roughened inner tapered surface on an inner periphery. The second barrel includes a second plunger, a screw tube portion with a female screw on an inner periphery thereof freely engageable with the male screw of the connecting tube portion, and a nozzle portion situated inside the screw tube portion with a non-roughened outer tapered surface fitting to the non-roughened inner tapered surface. A surface of the male screw and the outer periphery of the connecting tube portion, or a surface of the female screw and the inner periphery of the screw tube portion are roughened to a surface roughness in a range between Ra 1.0 and Ra 2.0 micrometer.

4 Claims, 5 Drawing Sheets

SYRINGE KIT FOR MIXING TWO MEDICINAL FLUIDS

RELATED APPLICATIONS

The present application is based on, and claims priority from, Japanese Application No. JP2011-283255 filed Dec. 26, 2011, the disclosure of which is hereby incorporated by reference herein in its entirety.

TECHNICAL FIELD

The present invention relates to a syringe kit for mixing two medicinal fluids or chemicals which is used for mixing a medicinal fluid in one barrel with a medicinal fluid in the other barrel.

BACKGROUND ART

It is generally known to use a so-called syringe kit for mixing two medicinal chemicals wherein a medicinal chemical contained in one barrel is mixed with a medicinal chemical contained in the other barrel by screwing together the tip portion of one barrel having a plunger and the tip portion of the other barrel having a plunger so as to communicate with each other (see Patent Document 1, for example).

Patent Document 1: Japanese Laid-open Patent Application, Tokuhyo 2003-518411

DISCLOSURE OF INVENTION

Problems to be Resolved by the Invention

In this type of syringe kits including a syringe kit for mixing two medicinal chemicals shown in Patent Document 1, the aforementioned one barrel and the other barrel are usually made of an injection-molded synthetic resin and have smooth mirror surfaces. Because of this configuration, a stick and slip phenomenon (a friction vibration phenomenon where the friction surfaces stick and slip repeatedly) tends to occur on the screwed surfaces when the tip portion of one barrel and the tip portion of the other barrel are screwed together before mixing two medicinal chemicals and therefore it becomes a cause of disturbing smooth and steady operations.

The present invention has been made in view of the problems in the prior art and provides a syringe kit for mixing two medicinal chemicals which can prevent stick and slip phenomena which tend to occur when the tip potion of one barrel and the tip portion of the other barrel are screwed together before mixing two medicinal chemicals.

Means for Solving the Problems

In order to resolve the aforementioned problems, a syringe kit for mixing two medicinal chemicals according to the present invention is constituted as a syringe kit for mixing two medicinal chemicals which is used for mixing a medicinal chemical in a first barrel and a medicinal chemical in a second barrel by connecting the tip portion of the first barrel having a plunger to the tip portion of the second barrel having a plunger so as to communicate with each other, wherein a connecting tube portion is formed at the tip portion of the first barrel, the outer periphery of the connecting tube portion has a male screw, the inner periphery of the connecting tube portion has an inner tapered surface, a screw tube portion and a nozzle portion are formed at the tip portion of the second barrel, the inner periphery of the screw tube portion has a female screw which is screwed together with the male screw on the outer periphery of the connecting tube portion in a freely removable manner, the outer periphery of the nozzle portion has an outer tapered surface which fits to the inner tapered surface on the inner periphery of the connecting tube portion, either the outer periphery of the connecting tube portion of the first barrel and the surface of the male screw or the inner periphery of the screw tube portion of the second barrel and the surface of the female screw is roughened, or both of them are roughened, so as to have a surface roughness in a range between Ra1.0 and Ra2.0, and therefore it is possible to prevent stick and slip phenomena between the two members.

In a syringe kit for mixing two medicinal chemicals according to the present invention, it is preferable to set the taper angle of the inner tapered surface of the connecting tube portion of the first barrel and the outer tapered surface of the nozzle portion of the second barrel to a range between 6% and 12% (a degree of taper representing the ratio of a change in diameter to a length by a percentage; it is also represented as 6-12/100), because the taper-fitted connection between the two members and the disengagement from the taper-fitted condition become smooth. Additionally, it is preferable to configure so that the tip portion of the nozzle portion is positioned in the connecting tube portion in a taper-fitted condition of the two members, because a gasket of the plunger of the first barrel can slide in the first barrel having a sufficient stroke when the medicinal chemical in the first barrel is mixed with the medicinal chemical in the second barrel.

In a syringe kit for mixing two medicinal chemicals according to the present invention, it is also preferable to form the first barrel and the second barrel by cyclic polyolefin which has a high transparency, a high steam sterilization property and a good medical agent non-absorption property.

Effect of Invention

In a syringe kit for mixing two medicinal chemicals according to the present invention, it is possible to prevent stick and slip phenomena which tend to occur when a male screw on the outer periphery of a connecting tube portion of a first barrel and a female screw on the inner periphery of a screw tube portion of a second barrel are screwed together or they are released from the screwed condition, and it is possible to ensure smooth and steady operations.

DETAILED DESCRIPTION OF THE INVENTION

One embodiment of a syringe kit for mixing two medicinal chemicals according to the present invention will be described below referring to the attached drawings. A syringe kit for mixing two medicinal chemicals according to one embodiment is used to mix a medicinal chemical A and a medicinal chemical B when necessary, for example.

Figure 1:
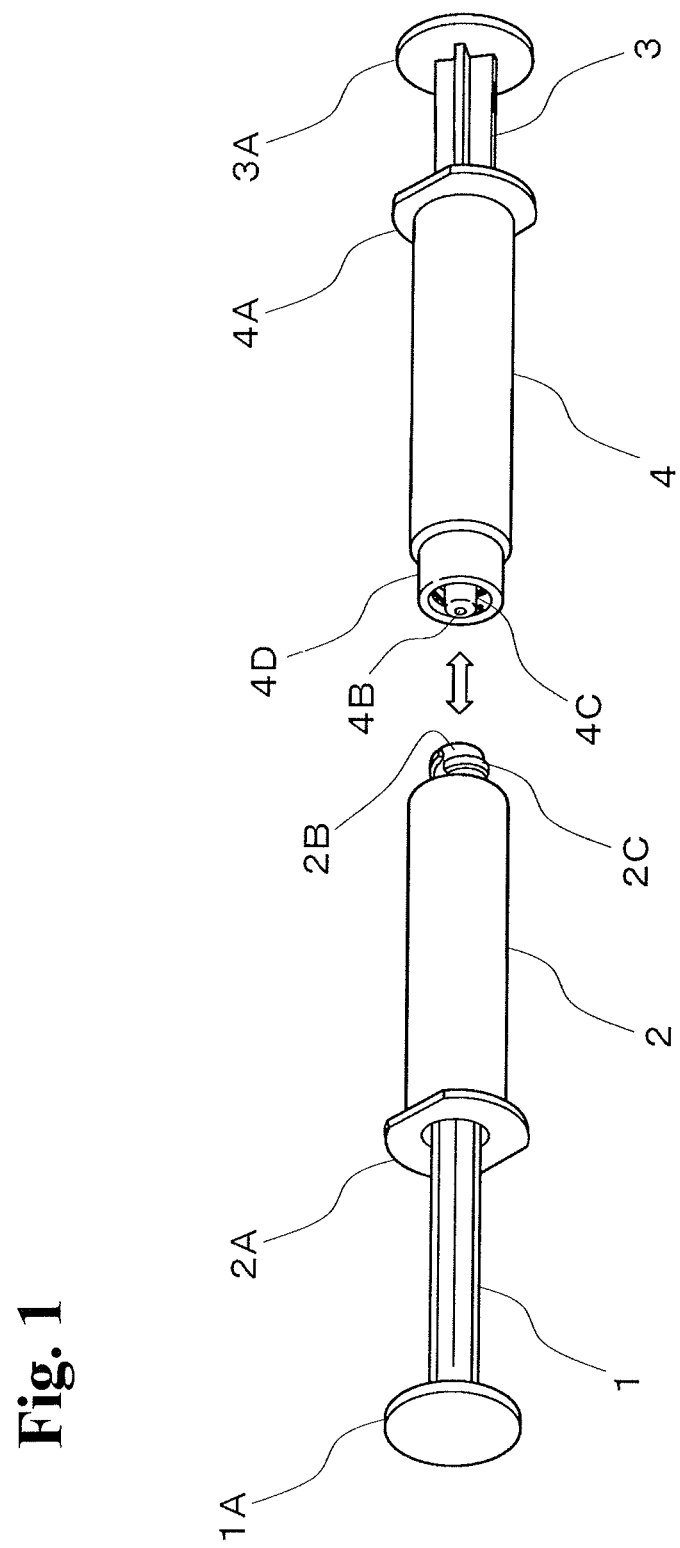
FIG. 1 shows an exploded perspective view showing a configuration of a syringe kit for mixing two medicinal chemicals according to one embodiment of the present invention.

As shown in FIG. 1, a syringe kit for mixing two medicinal chemicals according to one embodiment comprises a first barrel 2 (see FIGS. 2 and 3) and a second barrel 4 (see FIGS. 4 and 5), wherein a first plunger 1 is inserted into the first barrel 2 in a freely slidable manner and a medicinal chemical A is contained in the inner space in advance, and a second plunger 3 is inserted into the second barrel 4 in a freely slidable manner and a medicinal chemical B is contained in the inner space in advance.

The first plunger 1 has a gasket (not shown in drawings) and an end plate 1A, wherein the gasket is attached to the tip portion which faces the inner space of the first barrel 2 and the end plate 1A is formed at the rear end portion of the first plunger 1 which protrudes from the rear end portion of the first barrel 2. The second plunger 3 is similarly configured and the second plunger 3 has a gasket (not shown in drawings) at the tip portion which faces the inner space of the second barrel 4, and an end plate 3A is formed at the rear end portion of the second plunger 3 which protrudes from the rear end portion of the second barrel 4.

Although the material constituting the first barrel 2 is not limited to a specific material, it is preferable to use a material which is generally used for syringes, which is optically transparent and which has a grass transition point or a melting point of 110° C. or higher, for example, polypropylene, polymethylpentene, polyolefin like cyclic polyolefin, polyethylene terephthalate, polyethylene naphthalate, amorphous polyarylate, etc. Cyclic polyolefin is especially desirable in view of a high transparency, a high steam sterilization property and a good medical agent non-absorption property.

The first barrel 2 is integrally formed by one of the aforementioned various types of synthetic resins using injection-molding so that a flange 2A is formed at the rear end portion. Similarly, the second barrel 4 is integrally formed by one of the aforementioned various synthetic resins using injection-molding so that a flange 4A is formed at the rear end portion. The first barrel 2 and the second barrel 4 may be formed by either an identical synthetic resin or a similar type of synthetic resin (hereinafter, called as a similar type of synthetic resin) or different synthetic resins or different types of synthetic resins (hereinafter, called as different types of synthetic resins).

Figure 2:
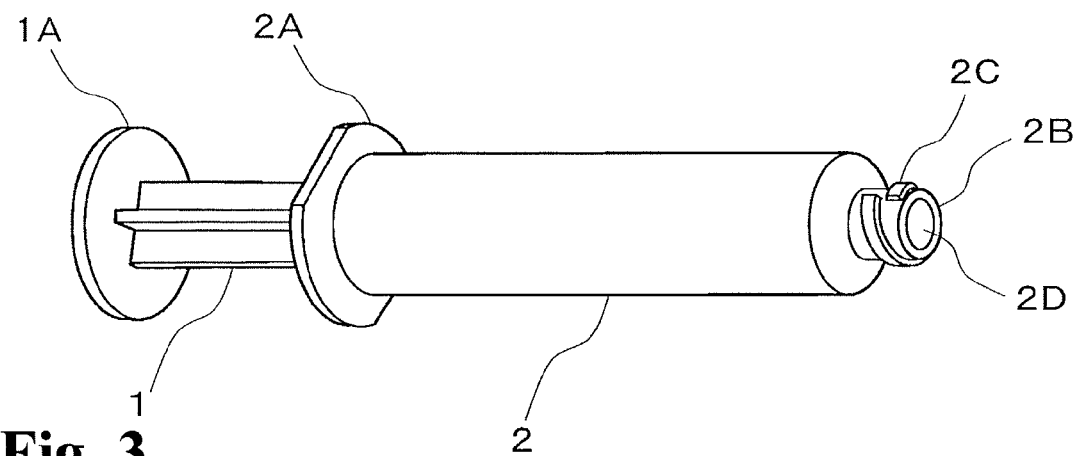
FIG. 2 shows an enlarged perspective view of the first plunger and the first barrel shown in FIG. 1.
Figure 3:
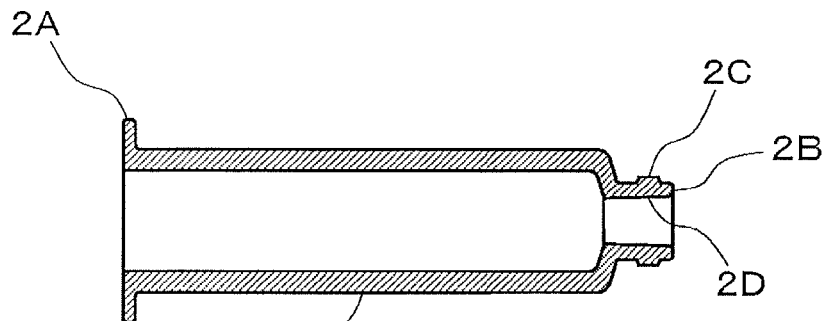
FIG. 3 shows a longitudinal cross-sectional view of the first barrel shown in FIG. 2.

Here, as shown in FIGS. 2 and 3, a connecting tube portion 2B is formed at the tip portion of the first barrel 2, and a male screw 2C is formed on the outer periphery of the connecting tube portion 2B. The male screw 2C is constituted as a trapezoidal screw with a large lead angle and a less winding number. An inner tapered surface 2D is formed on the inner periphery of the connecting tube portion 2B. The inner tapered surface 2D has a taper angle in a range between 6% and 12%, preferably in a range between 6% and 10%.

In general, nozzles of commercially supplied injectors have a taper (which corresponds to the outer tapered surface 4E according to the present invention) of about 6% usually. Therefore, it is preferable to set the taper angle of the inner tapered surface 2D to 6% because it is possible to connect a commercially supplied injector to the first barrel according to the present invention. In this case, the male screw 2C needs to have a shape and size which is suitable to screw together with a commercially supplied injector. Additionally, it is preferable to set the taper angle of the inner tapered surface 2D to a range between 6% and 10% as described above because it is possible to use a commercially supplied injector and the second barrel designed according to the present invention as well. Alternatively, it is effective in some applications to intentionally set the taper angle of the inner tapered surface 2D to an angle for which a commercially supplied injector cannot be used.

Figure 4:
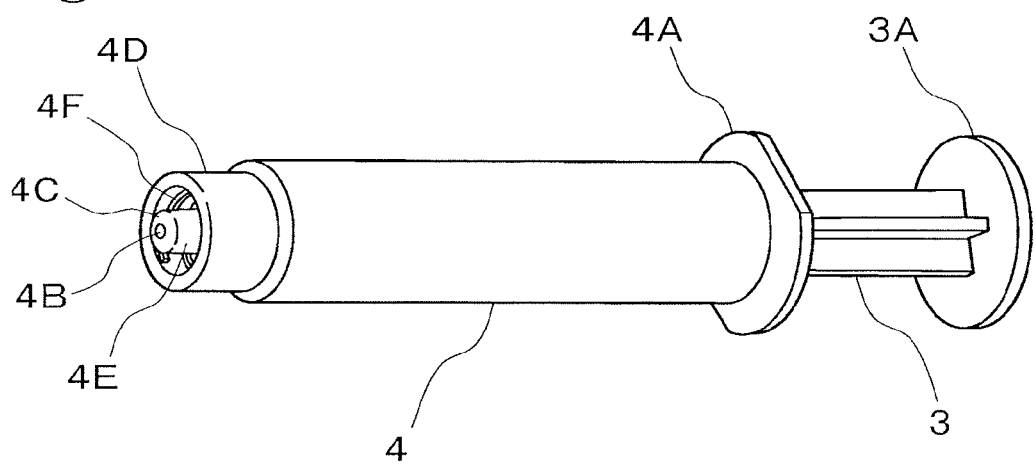
FIG. 4 shows an enlarged perspective view of the second plunger and the second barrel shown in FIG. 1.
Figure 5:
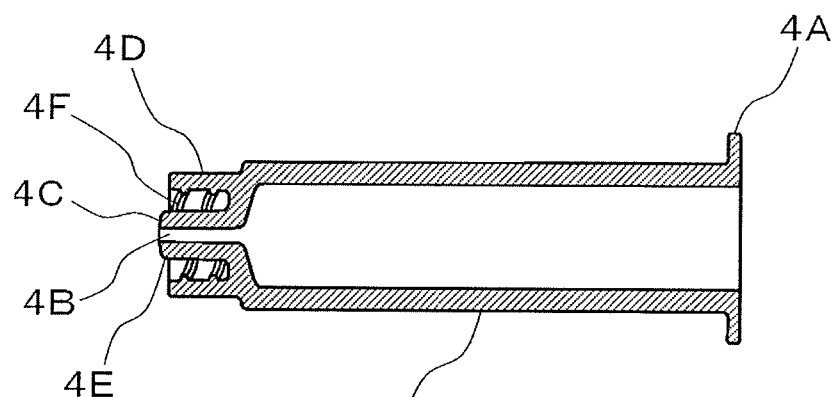
FIG. 5 shows a longitudinal cross-sectional view of the second barrel shown in FIG. 4.

On the other hand, as shown in FIGS. 4 and 5, a nozzle portion 4C having a center hole 4B is formed at the tip portion of the second barrel 4, and a screw tube portion 4D is formed at the external side of the nozzle portion 4C in a concentric fashion.

An outer tapered surface 4E is formed on the outer periphery of the nozzle portion 4C. The outer tapered surface 4E has the aforementioned taper angle and fits tightly and smoothly to the inner tapered surface 2D on the inner periphery of the connecting tube portion 2B. A female screw 4F is formed on the inner periphery of the screw tube portion 4D. The female screw 4F is screwed together with the male screw 2C on the outer surface of the connecting tube portion 2B in a freely removable manner. It is preferable to arrange so that the taper angle of the inner tapered surface 2D and that of the outer tapered surface 4E are concerted in view of a good sealing performance, however they do not need to be concerted always as described above.

Figure 6:
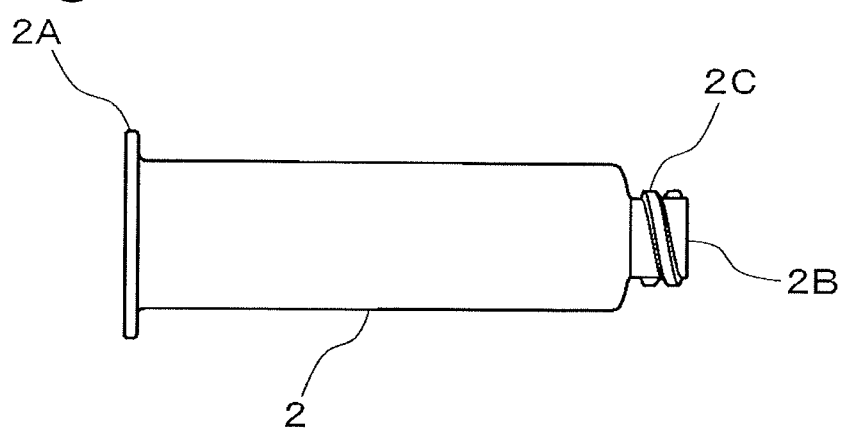
FIG. 6 shows a side view of the first barrel shown in FIG. 3.

Either one of the surface of the male screw 2C of the connecting tube portion 2B of the first barrel 2 and the surface of the female screw 4F of the screw tube portion 4D of the second barrel 4 is roughened to a predetermined surface roughness. In this embodiment, the surface of the female screw 4F of the screw tube portion 4D of the second barrel 4 is not roughened, whereas the surface of the male screw 2C and the outer periphery of the connecting tube portion 2B of the first barrel 2 shown in FIG. 6 are roughened to a surface roughness in a range between Ra1.0 and Ra2.0.

Figure 8:
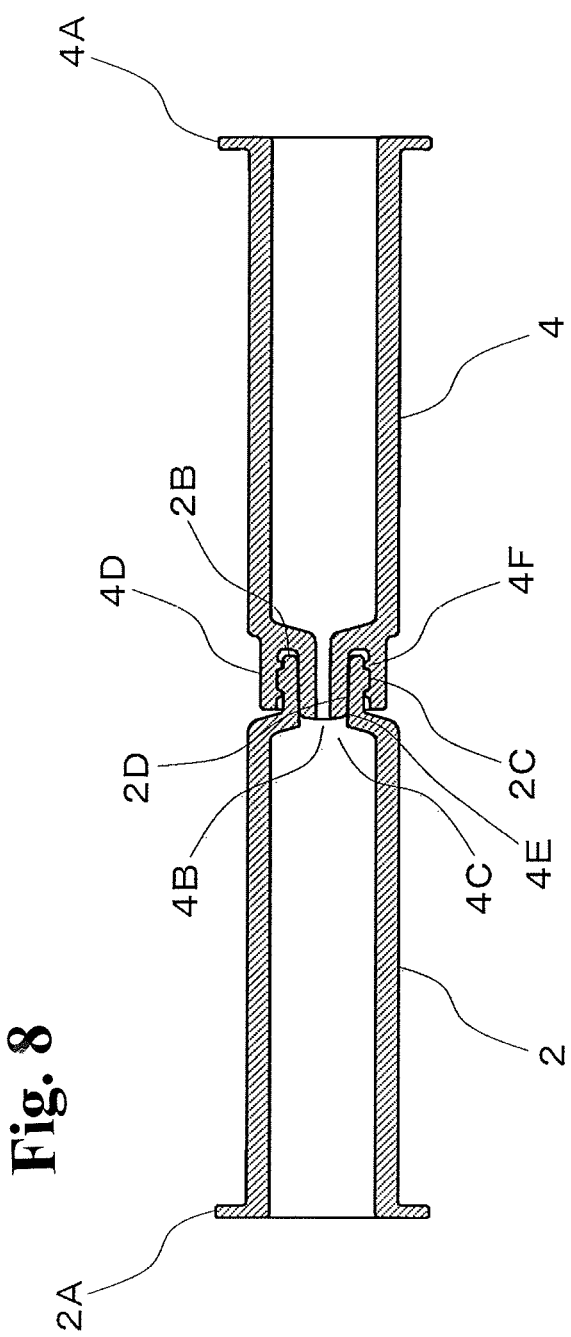
FIG. 8 shows a longitudinal cross-sectional view of the first barrel and the second barrel in a connected condition shown in FIG. 7.

Additionally, it is constituted so that the tip portion of the nozzle portion 4C of the second barrel 4 is positioned in the connection tube portion 2B of the first barrel 1 in a condition that the inner tapered surface 2D of the connecting tube portion 2B of the first barrel 2 and the outer tapered surface 4E of the nozzle portion 4C of the second barrel 4 are in a taper-fitted condition (see FIG. 8).

Figure 7:
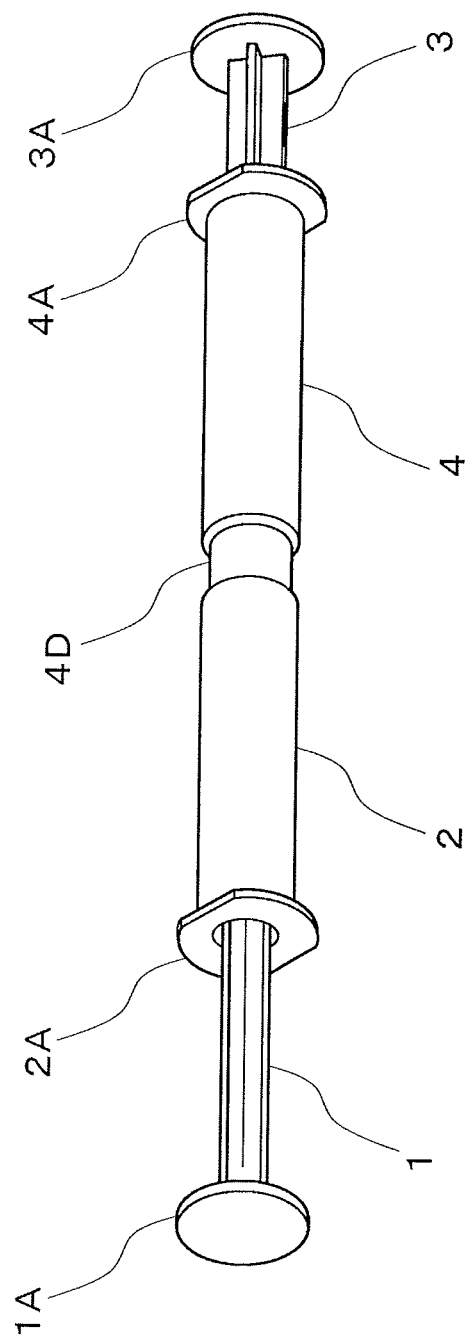
FIG. 7 shows a perspective view of a connected condition of a syringe kit for mixing two medicinal chemicals according to one embodiment.

In a syringe kit for mixing two medicinal chemicals according to one embodiment as described above, for example, when the medicinal chemical A in the first barrel 2 is mixed with the medicinal chemical B in the second barrel 4, the male screw 2C on the outer periphery of the connecting tube portion 2B of the first barrel 2 and the female screw 4F on the inner periphery of the screw tube portion 4D of the second barrel 4 shown in FIG. 1 are screwed together, and the inner tapered surface 2D on the inner periphery of the connecting tube portion 2B of the first barrel 2 and the outer tapered surface 4E on the outer periphery of the nozzle portion 4C of the second barrel 4 are taper-fitted (see FIG. 7).

During the operation, because either the surface of the male screw 2C and the outer periphery of the connecting tube portion 2B of the first barrel 2 or the surface of the female screw 4F and the inner periphery of the screw tube portion 4D of the second barrel 4 or both of them (in this embodiment, the surface of the male screw 2C of the connecting tube portion 2B of the first barrel 2) is roughened to a surface roughness in a range between Ra1.0 and Ra2.0, stick and slip phenomena are prevented. Additionally, it is preferable in view of a secured sealing performance to roughen neither the inner tapered surface 2D on the inner periphery of the connecting tube portion 2B of the first barrel 2 nor the outer tapered surface 4E of the nozzle portion 4C of the second barrel 4.

Therefore, in a syringe kit for mixing two medicinal chemicals according to one embodiment, it is possible to prevent stick and slip phenomena which tend to occur when the male screw 2C on the outer periphery of the connecting tube portion 2B of the first barrel 2 and the female screw 4F on the inner periphery of the screw tube portion 4D of the second barrel 4 are screwed together or they are released from a screwed condition, and thus it is possible to ensure a smooth and steady operation.

Additionally, in a syringe kit for mixing two medicinal chemicals according to one embodiment, the tip portion of the nozzle portion 4C of the second barrel 4 is positioned in the connecting tube portion 2B of the first barrel 2 in a condition that the inner tapered surface 2D on the inner periphery of the connecting tube portion 2B of the first barrel 2 and the outer tapered surface 4E on the outer periphery of the nozzle portion 4C of the second barrel 4 are taper-fitted (see FIG. 8). Thus, in a condition that the connecting tube portion 2B of the first barrel 2 is connected to the screw tube portion 4D of the second barrel 4 as shown in FIG. 7, the gasket of the first plunger 1 of the first barrel 2 can slide in the first barrel 2 with a sufficient stroke. As a result, it is possible to sufficiently and certainly mix the medicinal chemical A in the first barrel 2 with the medicinal chemical B in the second barrel 4.

A syringe kit for mixing two medicinal chemicals according to the present invention is not limited to the aforementioned embodiment. For example, it is possible to roughen only the surface of the female screw 4F and the inner periphery of the screw tube portion 4D of the second barrel 4 to a surface roughness in a range between Ra1.0 and Ra2.0 while the surface of the male screw 2C and the outer periphery of the connecting tube portion 2B of the first barrel 2 are not roughened. It is also possible to roughen both the surface of the male screw 2C and the outer periphery of the connecting tube portion 2B of the first barrel 2 and the surface of the female screw 4F and the inner periphery of the screw tube portion 4D of the second barrel 4. The most preferable embodiment is to roughen only the surface of the male screw 2C and the outer periphery of the connecting tube portion 2B of the first barrel 2. This embodiment can be used as a commercially supplied injector.

It is also possible to change the surface roughness for roughening within a range between Ra1.0 and Ra2.0 depending upon the type of synthetic resin which constitutes the first barrel 2 or the second barrel 4. By setting the surface roughness to this range, it successfully prevent stick and slip phenomena even when the first barrel 2 and the second barrel 4 are formed by either a same type of synthetic resin or different types of synthetic resins. It is impossible to effectively prevent stick and slip phenomena by using synthetic resins which is generally used for syringes if the surface roughness is less than Ra1.0. The screwed connection may be loosened because of a decreased screwed connection resistance during the mixing operation if the surface roughness is higher than Ra2.0.

EXPLANATION OF THE REFERENCE NUMBERS

1: first plunger
1A: end plate
2: first barrel
2A: flange
2B: connection tube portion
2C: male screw
2D: inner tapered surface
3: second plunger
3A: end plate
4: second barrel
4A: flange
4B: center hole
4C: nozzle portion
4D: screw tube portion
4E: outer tapered surface
4F: female screw

What is claimed is:

1. A syringe kit for mixing two medicinal fluids, comprising:
   a first barrel adapted to contain a medicinal fluid therein, and including a first plunger, and a connecting tube portion at a tip portion thereof having a male screw on an outer periphery thereof and a non-roughened inner tapered surface on an inner periphery thereof, and
   a second barrel adapted to contain another medicinal fluid therein, and including a second plunger, a screw tube portion with a female screw on an inner periphery thereof freely engageable with the male screw on the outer periphery of the connecting tube portion, and a nozzle portion situated inside the screw tube portion with a non-roughened outer tapered surface on an outer periphery thereof fitting to the non-roughened inner tapered surface on the inner periphery of the connecting tube portion to perform a secured seal between the inner periphery of the connecting tube portion and the outer periphery of the nozzle portion,
   wherein a surface of the male screw and the outer periphery of the connecting tube portion of the first barrel, and a surface of the female screw and the inner periphery of the screw tube portion of the second barrel are roughened to a surface roughness in a range between Ra1.0 and Ra2.0 micrometer,
   a length in a protrusion direction of the nozzle portion is shorter than that of the connecting tube portion so that when the first barrel and the second barrel are connected together, the nozzle portion is located inside the connecting tube portion to sufficiently and certainly mix the medicinal fluids in the first barrel and the second barrel, and
   the first barrel and the second barrel are made of cyclic polyolefin, respectively, to prevent stick and slip phenomenon between the connecting tube portion and the screw tube portion when the first barrel and the second barrel are connected together.

2. A syringe kit according to claim 1, wherein the non-roughened inner tapered surface of the connecting tube portion of the first barrel and the non-roughened outer tapered surface of the nozzle portion of the second barrel have a taper angle in a range between 6% and 12%, respectively, and the non-roughened inner tapered surface and the non-roughened outer tapered surface are fitted each other at the taper angle.

3. A syringe kit according to claim 1, wherein the first plunger has a first gasket arranged at a tip portion thereof and a first end plate arranged at a rear end portion thereof, and the second plunger has a second gasket arranged at a tip portion thereof and a second end plate arranged at a rear end portion thereof.

4. A syringe kit for mixing two medicinal fluids, comprising:

a first barrel adapted to contain a medicinal fluid therein, and including a first plunger, and a connecting tube portion at a tip portion thereof having a male screw on an outer periphery thereof and a non-roughened inner tapered surface on an inner periphery thereof, and a second barrel adapted to contain another medicinal fluid therein, and including a second plunger, a screw tube portion with a female screw on an inner periphery thereof freely engageable with the male screw on the outer periphery of the connecting tube portion, and a nozzle portion situated inside the screw tube portion with a non-roughened outer tapered surface on an outer periphery thereof fitting to the non-roughened inner tapered surface on the inner periphery of the connecting tube portion to perform a secured seal between the inner periphery of the connecting tube portion and the outer periphery of the nozzle portion, wherein a surface of the male screw and the outer periphery of the connecting tube portion of the first barrel are roughened to a surface roughness in a range between Ra1.0 and Ra2.0 micrometer, and a surface of the female screw and the inner periphery of the screw tube portion of the second barrel are not roughed, a length in a protrusion direction of the nozzle portion is shorter than that of the connecting tube portion so that when the first barrel and the second barrel are connected together, the nozzle portion is located inside the connecting tube portion to sufficiently and certainly mix the medicinal fluids in the first barrel and the second barrel, and the first barrel and the second barrel are made of cyclic polyolefin, respectively, to prevent stick and slip phenomenon between the connecting tube portion and the screw tube portion when the first barrel and the second barrel are connected together.

* * * * *